(12) United States Patent
Stone et al.

(10) Patent No.: US 8,273,106 B2
(45) Date of Patent: Sep. 25, 2012

(54) SOFT TISSUE REPAIR AND CONDUIT DEVICE

(75) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 12/976,328

(22) Filed: Dec. 22, 2010

(65) Prior Publication Data

US 2011/0087284 A1  Apr. 14, 2011

Related U.S. Application Data

(63) Continuation of application No. 11/869,440, filed on Oct. 9, 2007, now Pat. No. 7,857,830, which is a continuation-in-part of application No. 11/347,661, filed on Feb. 3, 2006, now Pat. No. 7,749,250, and a continuation-in-part of application No. 11/408,282, filed on Apr. 20, 2006, now abandoned.

(60) Provisional application No. 60/885,057, filed on Jan. 16, 2007, provisional application No. 60/885,062, filed on Jan. 16, 2007.

(51) Int. Cl.
*A61B 17/04* (2006.01)
*A61B 17/84* (2006.01)
*A61F 2/08* (2006.01)

(52) U.S. Cl. ......................... 606/232; 606/300

(58) Field of Classification Search .......... 606/300, 606/213, 215, 216, 232, 60, 74, 151; 623/13.11, 623/14.12
See application file for complete search history.

(56) References Cited

U.S. PATENT DOCUMENTS

| | | | |
|---|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 417,805 A | 12/1889 | Beaman |
| 487,304 A | 12/1892 | Todd |

(Continued)

FOREIGN PATENT DOCUMENTS

AU  4957264  3/1966

(Continued)

OTHER PUBLICATIONS

"Do your next distal tendon repair with . . . The Lubbers Technique", Teno Fix® brochure, 2003 (2 pages) Ortheon® Medical.

(Continued)

*Primary Examiner* — Dianne Dornbusch
(74) *Attorney, Agent, or Firm* — Harness, Dickey

(57) ABSTRACT

A soft tissue repair device includes a deformable tubular member having a longitudinal bore extending between first and second open ends and a flexible strand passing through the longitudinal bore of the tubular member. The flexible strand has a first end portion extending outside the first open end of the tubular member and a second portion forming a first loop that passes through the second open end of the tubular member and an intermediate opening between the first and second open ends of the tubular member. Pulling the first end portion of the flexible strand away from the tubular member deforms a portion of the tubular member between the second open end and the intermediate opening into a folded shape forming a soft tissue anchor.

22 Claims, 5 Drawing Sheets

U.S. PATENT DOCUMENTS

| | | |
|---|---|---|
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A * | 9/1971 | Barry ........................ 128/898 |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A * | 9/1977 | Barry ........................ 623/15.11 |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |

| | | |
|---|---|---|
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A * | 11/1991 | Gilbertson et al. .......... 623/2.37 |
| 5,074,874 A | 12/1991 | Yoon et al. |
| 5,078,731 A | 1/1992 | Hayhurst |
| 5,078,843 A | 1/1992 | Pratt |

| Patent | Date | Inventor |
|---|---|---|
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A * | 12/1993 | Hayhurst et al. ............... 606/232 |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |

| | | | | | |
|---|---|---|---|---|---|
| 5,470,337 A | 11/1995 | Moss | 5,632,748 A | 5/1997 | Beck, Jr. et al. |
| 5,470,338 A | 11/1995 | Whitfield et al. | 5,641,256 A | 6/1997 | Gundy |
| 5,472,452 A | 12/1995 | Trott | 5,643,266 A | 7/1997 | Li |
| 5,474,565 A | 12/1995 | Trott | 5,643,269 A | 7/1997 | Harle et al. |
| 5,474,568 A | 12/1995 | Scott | 5,643,295 A | 7/1997 | Yoon |
| 5,474,572 A | 12/1995 | Hayhurst | 5,643,319 A | 7/1997 | Green et al. |
| 5,478,344 A | 12/1995 | Stone et al. | 5,643,320 A | 7/1997 | Lower et al. |
| 5,478,345 A | 12/1995 | Stone et al. | 5,643,321 A | 7/1997 | McDevitt |
| 5,480,403 A | 1/1996 | Lee et al. | 5,645,546 A | 7/1997 | Fard |
| 5,480,406 A | 1/1996 | Nolan et al. | 5,645,547 A | 7/1997 | Coleman |
| 5,484,442 A | 1/1996 | Melker et al. | 5,645,568 A | 7/1997 | Chervitz et al. |
| 5,486,197 A | 1/1996 | Le et al. | 5,645,588 A | 7/1997 | Graf et al. |
| 5,490,750 A | 2/1996 | Gundy | 5,647,874 A | 7/1997 | Hayhurst |
| 5,496,331 A | 3/1996 | Xu et al. | 5,649,959 A | 7/1997 | Hannam et al. |
| 5,496,348 A | 3/1996 | Bonutti | 5,649,963 A | 7/1997 | McDevitt |
| 5,500,000 A | 3/1996 | Feagin et al. | 5,658,289 A | 8/1997 | Boucher et al. |
| 5,505,736 A | 4/1996 | Reimels et al. | 5,658,299 A | 8/1997 | Hart |
| 5,507,754 A | 4/1996 | Green et al. | 5,658,313 A | 8/1997 | Thal |
| 5,520,691 A | 5/1996 | Branch | 5,662,658 A | 9/1997 | Wenstrom, Jr. |
| 5,520,700 A | 5/1996 | Beyar et al. | 5,662,663 A | 9/1997 | Shallman |
| 5,520,702 A | 5/1996 | Sauer et al. | 5,662,681 A | 9/1997 | Nash et al. |
| 5,522,817 A | 6/1996 | Sander et al. | 5,665,112 A | 9/1997 | Thal |
| 5,522,820 A | 6/1996 | Caspari et al. | 5,667,513 A | 9/1997 | Torrie et al. |
| 5,522,844 A | 6/1996 | Johnson | 5,671,695 A | 9/1997 | Schroeder |
| 5,522,845 A | 6/1996 | Wenstrom, Jr. | 5,674,224 A | 10/1997 | Howell et al. |
| 5,522,846 A | 6/1996 | Bonutti | 5,679,723 A | 10/1997 | Cooper et al. |
| 5,524,946 A | 6/1996 | Thompson | 5,681,334 A * | 10/1997 | Evans et al. .................. 606/148 |
| 5,527,321 A | 6/1996 | Hinchliffe | 5,681,352 A | 10/1997 | Clancy, III et al. |
| 5,527,342 A | 6/1996 | Pietrzak et al. | 5,683,419 A | 11/1997 | Thal |
| 5,527,343 A | 6/1996 | Bonutti | 5,688,285 A | 11/1997 | Yamada et al. |
| 5,534,012 A | 7/1996 | Bonutti | 5,690,676 A | 11/1997 | DiPoto et al. |
| 5,536,270 A | 7/1996 | Songer et al. | 5,690,678 A | 11/1997 | Johnson |
| 5,540,698 A | 7/1996 | Preissman | 5,693,046 A | 12/1997 | Songer et al. |
| 5,540,703 A | 7/1996 | Barker, Jr. et al. | 5,695,497 A | 12/1997 | Stahelin et al. |
| 5,540,718 A | 7/1996 | Bartlett | 5,697,929 A | 12/1997 | Mellinger |
| 5,545,168 A | 8/1996 | Burke | 5,699,657 A | 12/1997 | Paulson |
| 5,545,178 A * | 8/1996 | Kensey et al. ................ 606/213 | 5,702,397 A | 12/1997 | Goble et al. |
| 5,545,180 A | 8/1996 | Le et al. | 5,702,422 A | 12/1997 | Stone |
| 5,545,228 A | 8/1996 | Kambin | 5,702,462 A | 12/1997 | Oberlander |
| 5,549,613 A | 8/1996 | Goble et al. | 5,707,373 A | 1/1998 | Sevrain et al. |
| 5,549,617 A | 8/1996 | Green et al. | 5,711,969 A | 1/1998 | Patel et al. |
| 5,549,619 A | 8/1996 | Peters et al. | 5,713,005 A | 1/1998 | Proebsting |
| 5,549,630 A | 8/1996 | Bonutti | 5,713,904 A | 2/1998 | Errico et al. |
| 5,549,631 A | 8/1996 | Bonutti | 5,713,905 A | 2/1998 | Goble et al. |
| 5,562,683 A | 10/1996 | Chan | 5,713,921 A | 2/1998 | Bonutti |
| 5,562,685 A | 10/1996 | Mollenauer et al. | 5,716,359 A | 2/1998 | Ojima et al. |
| 5,562,686 A | 10/1996 | Sauer et al. | 5,716,397 A * | 2/1998 | Myers .......................... 623/2.36 |
| 5,569,269 A | 10/1996 | Hart et al. | 5,718,717 A | 2/1998 | Bonutti |
| 5,569,305 A | 10/1996 | Bonutti | 5,720,747 A | 2/1998 | Burke |
| 5,571,090 A | 11/1996 | Sherts | 5,720,765 A | 2/1998 | Thal |
| 5,571,139 A | 11/1996 | Jenkins, Jr. | 5,720,766 A | 2/1998 | Zang et al. |
| 5,572,655 A | 11/1996 | Tuljapurkar et al. | 5,722,976 A | 3/1998 | Brown |
| 5,573,286 A | 11/1996 | Rogozinski | 5,725,549 A | 3/1998 | Lam |
| 5,573,542 A | 11/1996 | Stevens | 5,725,556 A | 3/1998 | Moser et al. |
| 5,573,548 A | 11/1996 | Nazre et al. | 5,725,581 A | 3/1998 | Brånemark et al. |
| 5,577,299 A | 11/1996 | Thompson et al. | 5,725,582 A | 3/1998 | Bevan et al. |
| 5,578,057 A | 11/1996 | Wenstrom, Jr. | 5,726,722 A | 3/1998 | Uehara et al. |
| 5,584,695 A | 12/1996 | Lal Sachdeva et al. | 5,728,107 A | 3/1998 | Zlock et al. |
| 5,584,835 A | 12/1996 | Greenfield | 5,728,109 A | 3/1998 | Schulze et al. |
| 5,584,836 A | 12/1996 | Ballintyn et al. | 5,728,136 A | 3/1998 | Thal |
| 5,584,862 A | 12/1996 | Bonutti | 5,733,293 A | 3/1998 | Scirica et al. |
| 5,586,986 A | 12/1996 | Hinchliffe | 5,733,306 A | 3/1998 | Bonutti |
| 5,588,575 A | 12/1996 | Davignon | 5,733,307 A | 3/1998 | Dinsdale |
| 5,591,180 A | 1/1997 | Hinchliffe | 5,735,875 A | 4/1998 | Bonutti et al. |
| 5,591,181 A | 1/1997 | Stone et al. | 5,741,259 A | 4/1998 | Chan |
| 5,591,207 A | 1/1997 | Coleman | 5,741,260 A | 4/1998 | Songer et al. |
| 5,593,407 A | 1/1997 | Reis et al. | 5,741,281 A | 4/1998 | Martin et al. |
| 5,593,425 A | 1/1997 | Bonutti et al. | 5,743,912 A | 4/1998 | Lahille et al. |
| 5,601,557 A | 2/1997 | Hayhurst | 5,746,751 A | 5/1998 | Sherts |
| 5,601,559 A | 2/1997 | Melker et al. | 5,746,752 A | 5/1998 | Burkhart |
| 5,601,571 A | 2/1997 | Moss | 5,746,754 A | 5/1998 | Chan |
| 5,603,716 A | 2/1997 | Morgan et al. | 5,749,898 A | 5/1998 | Schulze et al. |
| 5,607,429 A | 3/1997 | Hayano et al. | 5,755,729 A | 5/1998 | de la Torre et al. |
| 5,618,290 A | 4/1997 | Toy et al. | 5,755,791 A | 5/1998 | Whitson et al. |
| 5,626,611 A | 5/1997 | Liu et al. | 5,766,176 A | 6/1998 | Duncan |
| 5,626,614 A | 5/1997 | Hart | 5,766,218 A | 6/1998 | Arnott |
| 5,628,756 A | 5/1997 | Barker, Jr. et al. | 5,766,250 A | 6/1998 | Chervitz et al. |
| 5,628,766 A | 5/1997 | Johnson | 5,769,894 A | 6/1998 | Ferragamo |
| 5,630,824 A | 5/1997 | Hart | 5,769,899 A | 6/1998 | Schwartz et al. |

| | | | | | | |
|---|---|---|---|---|---|---|
| 5,772,673 A | 6/1998 | Cuny et al. | 5,968,077 A | 10/1999 | Wojciechowicz et al. | |
| 5,776,196 A | 7/1998 | Matsuzaki et al. | 5,972,006 A | 10/1999 | Sciaino, Jr. | |
| 5,782,845 A | 7/1998 | Shewchuk | 5,976,125 A | 11/1999 | Graham | |
| 5,782,862 A | 7/1998 | Bonutti | 5,976,127 A | 11/1999 | Lax | |
| 5,782,864 A | 7/1998 | Lizardi | 5,980,524 A | 11/1999 | Justin et al. | |
| 5,782,866 A | 7/1998 | Wenstrom, Jr. | 5,980,539 A | 11/1999 | Kontos | |
| 5,785,714 A | 7/1998 | Morgan et al. | 5,980,558 A | 11/1999 | Wiley | |
| 5,792,142 A | 8/1998 | Galitzer | 5,980,559 A | 11/1999 | Bonutti | |
| 5,792,149 A | 8/1998 | Sherts et al. | 5,989,252 A * | 11/1999 | Fumex | 606/232 |
| 5,796,127 A | 8/1998 | Hayafuji et al. | 5,989,256 A | 11/1999 | Kuslich et al. | |
| 5,797,915 A | 8/1998 | Pierson, III et al. | 5,989,282 A | 11/1999 | Bonutti | |
| 5,797,928 A | 8/1998 | Kogasaka | 5,993,452 A | 11/1999 | Vandewalle | |
| 5,800,407 A | 9/1998 | Eldor et al. | 5,993,476 A | 11/1999 | Groiso | |
| 5,810,824 A | 9/1998 | Chan | 5,997,542 A | 12/1999 | Burke | |
| 5,810,848 A | 9/1998 | Hayhurst | 5,997,552 A | 12/1999 | Person et al. | |
| 5,814,069 A | 9/1998 | Schulze et al. | 5,997,575 A | 12/1999 | Whitson et al. | |
| 5,814,070 A | 9/1998 | Borzone et al. | 6,001,100 A | 12/1999 | Sherman et al. | |
| 5,814,072 A | 9/1998 | Bonutti | 6,007,538 A | 12/1999 | Levin | |
| 5,814,073 A | 9/1998 | Bonutti | 6,007,567 A | 12/1999 | Bonutti | |
| 5,823,980 A | 10/1998 | Kopfer | 6,010,525 A | 1/2000 | Bonutti et al. | |
| 5,824,011 A | 10/1998 | Stone et al. | 6,016,727 A | 1/2000 | Morgan | |
| 5,830,234 A | 11/1998 | Wojciechowicz et al. | 6,022,352 A | 2/2000 | Vandewalle | |
| 5,843,084 A | 12/1998 | Hart et al. | 6,022,373 A | 2/2000 | Li | |
| 5,845,645 A | 12/1998 | Bonutti | 6,024,758 A | 2/2000 | Thal | |
| 5,846,254 A | 12/1998 | Schulze et al. | 6,027,523 A | 2/2000 | Schmieding | |
| 5,848,983 A | 12/1998 | Basaj et al. | 6,030,410 A | 2/2000 | Zurbrugg | |
| 5,849,012 A | 12/1998 | Abboudi | 6,033,429 A | 3/2000 | Magovern | |
| 5,860,973 A | 1/1999 | Michelson | 6,033,430 A | 3/2000 | Bonutti | |
| 5,868,740 A | 2/1999 | LeVeen et al. | 6,039,753 A | 3/2000 | Meislin | |
| 5,868,748 A | 2/1999 | Burke | 6,041,485 A | 3/2000 | Pedlick et al. | |
| 5,868,789 A | 2/1999 | Huebner | 6,042,601 A | 3/2000 | Smith | |
| 5,871,484 A | 2/1999 | Spievack et al. | 6,045,551 A | 4/2000 | Bonutti | |
| 5,871,486 A | 2/1999 | Huebner et al. | 6,045,571 A | 4/2000 | Hill et al. | |
| 5,871,490 A | 2/1999 | Schulze et al. | 6,045,572 A | 4/2000 | Johnson et al. | |
| 5,885,294 A | 3/1999 | Pedlick et al. | 6,045,573 A | 4/2000 | Wenstrom, Jr. et al. | |
| 5,891,168 A | 4/1999 | Thal | 6,045,574 A | 4/2000 | Thal | |
| 5,893,592 A | 4/1999 | Schulze et al. | 6,047,826 A | 4/2000 | Kalinski et al. | |
| 5,895,395 A | 4/1999 | Yeung | 6,048,343 A | 4/2000 | Mathis et al. | |
| 5,897,564 A | 4/1999 | Schulze et al. | 6,051,006 A | 4/2000 | Shluzas et al. | |
| 5,897,574 A | 4/1999 | Bonutti | 6,051,007 A | 4/2000 | Hogendijk et al. | |
| 5,899,902 A | 5/1999 | Brown et al. | 6,053,916 A | 4/2000 | Moore | |
| 5,899,938 A | 5/1999 | Sklar et al. | 6,053,921 A | 4/2000 | Wagner et al. | |
| 5,908,421 A | 6/1999 | Beger et al. | 6,056,752 A | 5/2000 | Roger et al. | |
| 5,908,436 A | 6/1999 | Cuschieri et al. | 6,056,772 A | 5/2000 | Bonutti | |
| 5,910,148 A | 6/1999 | Reimels et al. | 6,056,773 A | 5/2000 | Bonutti | |
| 5,911,721 A | 6/1999 | Nicholson et al. | 6,059,817 A | 5/2000 | Bonutti et al. | |
| 5,918,604 A | 7/1999 | Whelan | 6,059,818 A | 5/2000 | Johnson et al. | |
| 5,921,986 A | 7/1999 | Bonutti | 6,062,344 A | 5/2000 | Okabe et al. | |
| 5,925,008 A | 7/1999 | Douglas | 6,068,648 A | 5/2000 | Cole et al. | |
| 5,928,231 A | 7/1999 | Klein et al. | 6,071,305 A | 6/2000 | Brown et al. | |
| 5,928,267 A | 7/1999 | Bonutti et al. | 6,074,403 A | 6/2000 | Nord | |
| RE36,289 E | 8/1999 | Le et al. | 6,077,277 A | 6/2000 | Mollenauer et al. | |
| 5,931,838 A | 8/1999 | Vito | 6,077,292 A | 6/2000 | Bonutti | |
| 5,931,844 A | 8/1999 | Thompson et al. | 6,080,185 A | 6/2000 | Johnson et al. | |
| 5,931,869 A | 8/1999 | Boucher et al. | 6,086,591 A | 7/2000 | Bojarski | |
| 5,935,119 A | 8/1999 | Guy et al. | 6,086,592 A | 7/2000 | Rosenberg et al. | |
| 5,935,133 A | 8/1999 | Wagner et al. | 6,086,608 A | 7/2000 | Ek et al. | |
| 5,935,149 A | 8/1999 | Ek | 6,093,200 A | 7/2000 | Liu et al. | |
| 5,938,668 A | 8/1999 | Scirica et al. | 6,096,060 A | 8/2000 | Fitts et al. | |
| 5,941,439 A | 8/1999 | Kammerer et al. | 6,099,527 A | 8/2000 | Hochschuler et al. | |
| 5,941,900 A | 8/1999 | Bonutti | 6,099,530 A | 8/2000 | Simonian et al. | |
| 5,944,739 A | 8/1999 | Zlock et al. | 6,099,568 A | 8/2000 | Simonian et al. | |
| 5,946,783 A | 9/1999 | Plociennik et al. | 6,106,545 A | 8/2000 | Egan | |
| 5,947,915 A | 9/1999 | Thibodo, Jr. | 6,110,128 A | 8/2000 | Andelin et al. | |
| 5,947,982 A | 9/1999 | Duran | 6,117,160 A | 9/2000 | Bonutti | |
| 5,947,999 A | 9/1999 | Groiso | 6,117,162 A | 9/2000 | Schmieding et al. | |
| 5,948,002 A | 9/1999 | Bonutti | 6,123,710 A | 9/2000 | Pinczewski et al. | |
| 5,951,559 A | 9/1999 | Burkhart | 6,132,433 A | 10/2000 | Whelan | |
| 5,951,560 A | 9/1999 | Simon et al. | 6,132,437 A | 10/2000 | Omurtag et al. | |
| 5,954,747 A | 9/1999 | Clark | 6,139,565 A | 10/2000 | Stone et al. | |
| 5,957,953 A | 9/1999 | DiPoto et al. | RE36,974 E | 11/2000 | Bonutti | |
| 5,961,521 A | 10/1999 | Roger et al. | 6,143,017 A | 11/2000 | Thal | |
| 5,961,524 A | 10/1999 | Crombie | 6,146,406 A | 11/2000 | Shluzas et al. | |
| 5,964,764 A | 10/1999 | West, Jr. et al. | 6,146,408 A | 11/2000 | Bartlett | |
| 5,964,767 A | 10/1999 | Tapia et al. | 6,149,653 A | 11/2000 | Deslauriers | |
| 5,964,769 A | 10/1999 | Wagner et al. | 6,149,669 A | 11/2000 | Li | |
| 5,964,783 A | 10/1999 | Grafton et al. | 6,152,928 A | 11/2000 | Wenstrom, Jr. | |
| 5,968,045 A | 10/1999 | Frazier | 6,152,934 A | 11/2000 | Harper et al. | |
| 5,968,047 A | 10/1999 | Reed | 6,152,936 A | 11/2000 | Christy et al. | |

| | | | | | | |
|---|---|---|---|---|---|---|
| 6,152,949 | A | 11/2000 | Bonutti | 6,447,516 | B1 | 9/2002 | Bonutti |
| 6,156,039 | A | 12/2000 | Thal | 6,451,030 | B2 | 9/2002 | Li et al. |
| 6,156,056 | A | 12/2000 | Kearns et al. | 6,454,768 | B1 | 9/2002 | Jackson |
| 6,159,234 | A | 12/2000 | Bonutti et al. | 6,458,134 | B1 | 10/2002 | Songer et al. |
| 6,165,203 | A | 12/2000 | Krebs | 6,461,373 | B2 | 10/2002 | Wyman et al. |
| 6,168,598 | B1 | 1/2001 | Martello | 6,464,713 | B2 | 10/2002 | Bonutti |
| 6,168,628 | B1 | 1/2001 | Huebner | 6,468,293 | B2 | 10/2002 | Bonutti et al. |
| 6,179,840 | B1 | 1/2001 | Bowman | 6,471,707 | B1 | 10/2002 | Miller et al. |
| 6,183,461 | B1 | 2/2001 | Matsuura et al. | 6,475,230 | B1 * | 11/2002 | Bonutti et al. ................ 606/232 |
| 6,187,025 | B1 | 2/2001 | Machek | 6,482,210 | B1 | 11/2002 | Skiba et al. |
| 6,190,401 | B1 | 2/2001 | Green et al. | 6,485,504 | B1 * | 11/2002 | Johnson et al. ............... 606/216 |
| 6,190,411 | B1 | 2/2001 | Lo et al. | 6,491,714 | B1 | 12/2002 | Bennett |
| 6,193,754 | B1 | 2/2001 | Seedhom et al. | 6,497,901 | B1 | 12/2002 | Royer |
| 6,200,318 | B1 | 3/2001 | Har-Shai et al. | 6,500,184 | B1 | 12/2002 | Chan et al. |
| 6,200,329 | B1 | 3/2001 | Fung et al. | 6,500,195 | B2 | 12/2002 | Bonutti |
| 6,200,330 | B1 | 3/2001 | Benderev et al. | RE37,963 | E | 1/2003 | Thal |
| 6,203,556 | B1 | 3/2001 | Evans et al. | 6,503,267 | B2 | 1/2003 | Bonutti et al. |
| 6,203,565 | B1 | 3/2001 | Bonutti et al. | 6,506,190 | B1 | 1/2003 | Walshe |
| 6,203,572 | B1 | 3/2001 | Johnson et al. | 6,508,820 | B2 | 1/2003 | Bales |
| 6,206,883 | B1 | 3/2001 | Tunc | 6,508,821 | B1 | 1/2003 | Schwartz et al. |
| 6,210,376 | B1 | 4/2001 | Grayson | 6,508,830 | B2 | 1/2003 | Steiner |
| 6,214,012 | B1 | 4/2001 | Karpman et al. | 6,511,498 | B1 * | 1/2003 | Fumex ......................... 606/232 |
| 6,217,580 | B1 | 4/2001 | Levin | 6,511,499 | B2 | 1/2003 | Schmieding et al. |
| 6,221,107 | B1 | 4/2001 | Steiner et al. | 6,517,542 | B1 | 2/2003 | Papay et al. |
| 6,228,096 | B1 | 5/2001 | Marchand | 6,517,552 | B1 | 2/2003 | Nord et al. |
| 6,231,592 | B1 | 5/2001 | Bonutti et al. | 6,517,578 | B2 * | 2/2003 | Hein ........................ 623/13.13 |
| 6,235,057 | B1 | 5/2001 | Roger et al. | 6,517,579 | B1 | 2/2003 | Paulos et al. |
| 6,238,395 | B1 | 5/2001 | Bonutti | 6,520,964 | B2 | 2/2003 | Tallarida et al. |
| 6,241,734 | B1 | 6/2001 | Scribner et al. | 6,520,980 | B1 | 2/2003 | Foerster |
| 6,241,747 | B1 | 6/2001 | Ruff | 6,524,317 | B1 | 2/2003 | Ritchart et al. |
| 6,241,771 | B1 | 6/2001 | Gresser et al. | 6,527,777 | B2 | 3/2003 | Justin |
| 6,245,081 | B1 | 6/2001 | Bowman et al. | 6,527,794 | B1 | 3/2003 | McDevitt et al. |
| 6,258,091 | B1 | 7/2001 | Sevrain et al. | 6,527,795 | B1 | 3/2003 | Lizardi |
| 6,267,766 | B1 | 7/2001 | Burkhart | 6,533,795 | B1 | 3/2003 | Tran et al. |
| 6,269,716 | B1 | 8/2001 | Amis | 6,533,802 | B2 | 3/2003 | Bojarski et al. |
| 6,270,518 | B1 | 8/2001 | Pedlick et al. | 6,537,319 | B2 | 3/2003 | Whelan |
| 6,273,890 | B1 | 8/2001 | Frazier | 6,540,750 | B2 | 4/2003 | Burkhart |
| 6,280,474 | B1 | 8/2001 | Cassidy et al. | 6,540,769 | B1 | 4/2003 | Miller, III |
| 6,283,973 | B1 | 9/2001 | Hubbard et al. | 6,540,770 | B1 | 4/2003 | Tornier et al. |
| 6,283,996 | B1 | 9/2001 | Chervitz et al. | 6,544,281 | B2 | 4/2003 | ElAttrache et al. |
| 6,287,307 | B1 | 9/2001 | Abboudi | 6,547,564 | B1 | 4/2003 | Hansson et al. |
| 6,287,325 | B1 | 9/2001 | Bonutti | 6,547,800 | B2 | 4/2003 | Foerster et al. |
| 6,293,961 | B2 | 9/2001 | Schwartz et al. | 6,551,330 | B1 | 4/2003 | Bain et al. |
| 6,296,659 | B1 | 10/2001 | Foerster | 6,551,343 | B1 | 4/2003 | Tormala et al. |
| 6,299,615 | B1 | 10/2001 | Huebner | 6,553,802 | B1 | 4/2003 | Jacob et al. |
| 6,302,888 | B1 | 10/2001 | Mellinger et al. | 6,554,830 | B1 | 4/2003 | Chappius |
| 6,302,899 | B1 | 10/2001 | Johnson et al. | 6,554,852 | B1 | 4/2003 | Oberlander |
| 6,306,156 | B1 | 10/2001 | Clark | 6,554,862 | B2 | 4/2003 | Hays et al. |
| 6,306,159 | B1 | 10/2001 | Schwartz et al. | 6,562,071 | B2 | 5/2003 | Jarvinen et al. |
| 6,309,405 | B1 | 10/2001 | Bonutti | 6,565,572 | B2 | 5/2003 | Chappius |
| 6,312,448 | B1 | 11/2001 | Bonutti | 6,565,573 | B1 | 5/2003 | Ferrante et al. |
| 6,315,788 | B1 | 11/2001 | Roby | 6,569,186 | B1 | 5/2003 | Winters et al. |
| 6,319,271 | B1 | 11/2001 | Schwartz et al. | 6,569,187 | B1 | 5/2003 | Bonutti et al. |
| 6,328,758 | B1 | 12/2001 | Tornier et al. | 6,572,635 | B1 | 6/2003 | Bonutti |
| 6,342,060 | B1 | 1/2002 | Adams | 6,575,925 | B1 | 6/2003 | Noble |
| 6,343,531 | B2 | 2/2002 | Amis | 6,579,295 | B1 | 6/2003 | Supinski |
| 6,358,270 | B1 | 3/2002 | Lemer | 6,582,453 | B1 | 6/2003 | Tran et al. |
| 6,364,897 | B1 | 4/2002 | Bonutti | 6,585,730 | B1 | 7/2003 | Foerster |
| 6,368,322 | B1 | 4/2002 | Luks et al. | 6,585,740 | B2 | 7/2003 | Schlapfer et al. |
| 6,368,326 | B1 | 4/2002 | Dakin et al. | 6,585,750 | B2 | 7/2003 | Bonutti et al. |
| 6,368,343 | B1 | 4/2002 | Bonutti et al. | 6,589,245 | B1 | 7/2003 | Weiler et al. |
| 6,371,124 | B1 | 4/2002 | Whelan | 6,589,246 | B1 | 7/2003 | Hack et al. |
| 6,379,361 | B1 | 4/2002 | Beck, Jr. et al. | 6,592,609 | B1 | 7/2003 | Bonutti |
| 6,383,190 | B1 | 5/2002 | Preissman | 6,595,911 | B2 | 7/2003 | LoVuolo |
| 6,383,199 | B2 | 5/2002 | Carter et al. | 6,599,289 | B1 | 7/2003 | Bojarski et al. |
| 6,387,113 | B1 | 5/2002 | Hawkins et al. | 6,605,096 | B1 | 8/2003 | Ritchart |
| 6,387,129 | B2 | 5/2002 | Rieser et al. | 6,607,548 | B2 | 8/2003 | Pohjonen et al. |
| 6,391,030 | B1 | 5/2002 | Wagner et al. | 6,610,079 | B1 | 8/2003 | Li et al. |
| 6,398,785 | B2 | 6/2002 | Carchidi et al. | 6,613,018 | B2 | 9/2003 | Bagga et al. |
| 6,406,479 | B1 | 6/2002 | Justin et al. | 6,616,694 | B1 | 9/2003 | Hart |
| 6,409,743 | B1 | 6/2002 | Fenton, Jr. | 6,620,166 | B1 | 9/2003 | Wenstrom, Jr. et al. |
| 6,413,260 | B1 | 7/2002 | Berrevoets et al. | 6,620,185 | B1 | 9/2003 | Harvie et al. |
| 6,423,088 | B1 | 7/2002 | Fenton, Jr. | 6,620,195 | B2 | 9/2003 | Goble et al. |
| 6,428,562 | B2 | 8/2002 | Bonutti | 6,620,329 | B2 | 9/2003 | Rosen et al. |
| 6,432,123 | B2 | 8/2002 | Schwartz et al. | 6,620,349 | B1 | 9/2003 | Lopez |
| 6,436,123 | B1 | 8/2002 | Magovern | 6,623,492 | B1 | 9/2003 | Berube et al. |
| 6,436,124 | B1 | 8/2002 | Anderson et al. | 6,623,524 | B2 | 9/2003 | Schmieding |
| 6,440,134 | B1 | 8/2002 | Zaccherotti et al. | 6,626,910 | B1 | 9/2003 | Hugues et al. |
| 6,440,136 | B1 | 8/2002 | Gambale et al. | 6,626,919 | B1 | 9/2003 | Swanstrom |

| | | | | | | |
|---|---|---|---|---|---|---|
| 6,629,977 B1 | 10/2003 | Wolf | | 6,989,034 B2 | 1/2006 | Hammer et al. |
| 6,635,073 B2 | 10/2003 | Bonutti | | 7,001,429 B2 | 2/2006 | Ferguson |
| 6,638,279 B2 | 10/2003 | Bonutti | | 7,004,959 B2 | 2/2006 | Bonutti |
| 6,638,312 B2 | 10/2003 | Plouhar et al. | | 7,048,754 B2 | 5/2006 | Martin et al. |
| 6,641,596 B1 | 11/2003 | Lizardi | | 7,052,499 B2 | 5/2006 | Steger et al. |
| 6,641,597 B2 | 11/2003 | Burkhart et al. | | 7,066,942 B2 | 6/2006 | Treace |
| 6,645,227 B2 | 11/2003 | Fallin et al. | | 7,066,944 B2 | 6/2006 | Laufer et al. |
| 6,652,450 B2 | 11/2003 | Neisz et al. | | 7,081,126 B2 | 7/2006 | McDevitt et al. |
| 6,652,562 B2 | 11/2003 | Collier et al. | | 7,087,064 B1 | 8/2006 | Hyde |
| 6,652,563 B2 | 11/2003 | Dreyfuss | | 7,105,010 B2 | 9/2006 | Hart et al. |
| 6,656,182 B1 | 12/2003 | Hayhurst | | 7,112,221 B2 | 9/2006 | Harris et al. |
| 6,656,183 B2 | 12/2003 | Colleran et al. | | 7,118,583 B2 | 10/2006 | O'Quinn et al. |
| 6,658,182 B1 | 12/2003 | Gonthier et al. | | 7,131,467 B2 | 11/2006 | Gao et al. |
| 6,660,008 B1 | 12/2003 | Foerster et al. | | 7,137,996 B2 | 11/2006 | Steiner et al. |
| 6,660,022 B1 | 12/2003 | Li et al. | | 7,141,066 B2 | 11/2006 | Steiner et al. |
| 6,663,634 B2 | 12/2003 | Ahrens et al. | | 7,144,414 B2 | 12/2006 | Harvie et al. |
| 6,663,656 B2 | 12/2003 | Schmieding et al. | | 7,153,127 B2 | 12/2006 | Struble et al. |
| 6,666,868 B2 | 12/2003 | Fallin | | 7,153,307 B2 | 12/2006 | Scribner et al. |
| 6,682,533 B1 | 1/2004 | Dinsdale et al. | | 7,153,312 B1 | 12/2006 | Torrie et al. |
| 6,682,549 B2 | 1/2004 | Bartlett | | 7,153,327 B1 | 12/2006 | Metzger |
| 6,685,728 B2 | 2/2004 | Sinnott et al. | | 7,160,333 B2 | 1/2007 | Plouhar et al. |
| 6,689,137 B2 | 2/2004 | Reed | | 7,201,722 B2 | 4/2007 | Krueger |
| 6,689,153 B1 | 2/2004 | Skiba | | 7,255,675 B2 | 8/2007 | Gertner et al. |
| 6,689,154 B2 | 2/2004 | Bartlett | | 7,255,715 B2 | 8/2007 | Metzger |
| 6,692,499 B2 | 2/2004 | Tormala et al. | | 7,261,716 B2 | 8/2007 | Strobel et al. |
| 6,692,516 B2 | 2/2004 | West, Jr. et al. | | 7,264,634 B2 | 9/2007 | Schmieding |
| 6,712,849 B2 | 3/2004 | Re et al. | | 7,285,124 B2 | 10/2007 | Foerster |
| 6,716,224 B2 | 4/2004 | Singhatat | | 7,303,577 B1 | 12/2007 | Dean |
| 6,716,957 B2 | 4/2004 | Tunc | | 7,306,417 B2 | 12/2007 | Dorstewitz |
| 6,730,092 B2 | 5/2004 | Songer | | 7,326,222 B2 | 2/2008 | Dreyfuss et al. |
| 6,730,124 B2 | 5/2004 | Steiner | | 7,329,272 B2 | 2/2008 | Burkhart et al. |
| 6,736,799 B1 | 5/2004 | Erbe et al. | | 7,361,179 B2 | 4/2008 | Rousseau et al. |
| 6,737,053 B1 | 5/2004 | Goh et al. | | 7,377,845 B2 | 5/2008 | Stewart et al. |
| 6,746,483 B1 | 6/2004 | Bojarski et al. | | 7,390,329 B2 | 6/2008 | Westra et al. |
| 6,752,810 B1 | 6/2004 | Gao et al. | | 7,390,332 B2 | 6/2008 | Selvitelli et al. |
| 6,752,831 B2 | 6/2004 | Sybert et al. | | 7,399,018 B1 | 7/2008 | Khachaturian |
| 6,755,836 B1 | 6/2004 | Lewis | | 7,442,210 B2 * | 10/2008 | Segal et al. ................ 623/17.12 |
| 6,761,739 B2 | 7/2004 | Shepard | | 7,465,308 B2 | 12/2008 | Sikora et al. |
| 6,767,037 B2 | 7/2004 | Wenstrom, Jr. | | 7,494,506 B2 | 2/2009 | Brulez et al. |
| 6,770,076 B2 | 8/2004 | Foerster | | 7,513,910 B2 | 4/2009 | Buskirk et al. |
| 6,770,084 B1 | 8/2004 | Bain et al. | | 7,578,825 B2 | 8/2009 | Huebner |
| 6,773,450 B2 | 8/2004 | Leung et al. | | 7,585,311 B2 | 9/2009 | Green et al. |
| 6,779,701 B2 | 8/2004 | Bailly et al. | | 7,601,165 B2 | 10/2009 | Stone |
| 6,780,190 B2 | 8/2004 | Maroney | | 7,608,098 B1 | 10/2009 | Stone et al. |
| 6,780,198 B1 | 8/2004 | Gregoire et al. | | 7,615,076 B2 | 11/2009 | Cauthen, III et al. |
| 6,802,862 B1 | 10/2004 | Roger et al. | | 7,632,287 B2 | 12/2009 | Baker et al. |
| 6,808,502 B2 | 10/2004 | Nguyen et al. | | 7,651,509 B2 | 1/2010 | Bojarski et al. |
| 6,808,526 B1 | 10/2004 | Magerl et al. | | 7,658,750 B2 | 2/2010 | Li |
| 6,814,741 B2 | 11/2004 | Bowman et al. | | 7,658,751 B2 | 2/2010 | Stone et al. |
| 6,830,572 B2 | 12/2004 | McDevitt et al. | | 7,670,279 B2 | 3/2010 | Gertner |
| 6,833,005 B1 | 12/2004 | Mantas et al. | | 7,678,123 B2 | 3/2010 | Chanduszko |
| 6,840,953 B2 | 1/2005 | Martinek | | 7,695,493 B2 | 4/2010 | Saadat et al. |
| 6,860,885 B2 | 3/2005 | Bonutti | | 7,736,379 B2 | 6/2010 | Ewers et al. |
| 6,863,671 B1 | 3/2005 | Strobel et al. | | 7,758,594 B2 | 7/2010 | Lamson et al. |
| 6,872,040 B2 | 3/2005 | Deeg et al. | | 7,776,041 B1 | 8/2010 | Walters |
| 6,872,210 B2 | 3/2005 | Hearn | | 7,819,895 B2 | 10/2010 | Ginn et al. |
| 6,875,216 B2 | 4/2005 | Wolf | | 7,875,058 B2 | 1/2011 | Holmes, Jr. |
| 6,884,249 B2 | 4/2005 | May et al. | | 7,981,140 B2 | 7/2011 | Burkhart |
| 6,887,259 B2 | 5/2005 | Lizardi | | 7,998,203 B2 | 8/2011 | Blum |
| 6,890,354 B2 | 5/2005 | Steiner et al. | | 8,062,334 B2 | 11/2011 | Green et al. |
| 6,893,448 B2 | 5/2005 | O'Quinn et al. | | 8,075,574 B2 | 12/2011 | May et al. |
| 6,896,686 B2 | 5/2005 | Weber | | 8,167,906 B2 | 5/2012 | Cauldwell et al. |
| 6,899,722 B2 | 5/2005 | Bonutti | | 2001/0010005 A1 | 7/2001 | Kammerer et al. |
| 6,902,573 B2 | 6/2005 | Strobel et al. | | 2001/0014825 A1 | 8/2001 | Burke et al. |
| 6,905,513 B1 | 6/2005 | Metzger | | 2001/0019649 A1 | 9/2001 | Field et al. |
| 6,908,466 B1 | 6/2005 | Bonutti et al. | | 2001/0037131 A1 | 11/2001 | Schmieding et al. |
| 6,916,292 B2 | 7/2005 | Morawski et al. | | 2001/0037153 A1 | 11/2001 | Rockwood et al. |
| 6,916,321 B2 | 7/2005 | TenHuisen et al. | | 2001/0041916 A1 | 11/2001 | Bonutti |
| 6,921,402 B2 | 7/2005 | Contiliano et al. | | 2001/0041937 A1 | 11/2001 | Rieser et al. |
| 6,923,823 B1 | 8/2005 | Bartlett et al. | | 2001/0041938 A1 | 11/2001 | Hein |
| 6,923,824 B2 * | 8/2005 | Morgan et al. ................ 606/232 | | 2001/0044639 A1 | 11/2001 | Levinson |
| 6,951,565 B2 | 10/2005 | Keane et al. | | 2001/0047206 A1 | 11/2001 | Sklar et al. |
| 6,966,887 B1 * | 11/2005 | Chin ................ 604/8 | | 2001/0051816 A1 | 12/2001 | Enzerink et al. |
| 6,966,916 B2 | 11/2005 | Kumar | | 2001/0053934 A1 | 12/2001 | Schmieding |
| 6,969,391 B1 | 11/2005 | Gazzani | | 2002/0001964 A1 | 1/2002 | Choi |
| 6,969,398 B2 | 11/2005 | Stevens et al. | | 2002/0004669 A1 | 1/2002 | Bartlett |
| 6,972,027 B2 | 12/2005 | Fallin et al. | | 2002/0007182 A1 | 1/2002 | Kim |
| 6,980,903 B2 | 12/2005 | Daniels et al. | | 2002/0010513 A1 | 1/2002 | Schmieding |
| 6,986,781 B2 | 1/2006 | Smith | | 2002/0013607 A1 | 1/2002 | Lemer |

| | | | | | | |
|---|---|---|---|---|---|---|
| 2002/0013608 A1 | 1/2002 | ElAttrache et al. | | 2004/0133211 A1 | 7/2004 | Raskin et al. |
| 2002/0019649 A1* | 2/2002 | Sikora et al. ............... 606/232 | | 2004/0138664 A1 | 7/2004 | Bowman |
| 2002/0029066 A1 | 3/2002 | Foerster | | 2004/0138683 A1 | 7/2004 | Shelton et al. |
| 2002/0032465 A1 | 3/2002 | Lemer | | 2004/0138704 A1 | 7/2004 | Gambale et al. |
| 2002/0055780 A1 | 5/2002 | Sklar | | 2004/0138706 A1 | 7/2004 | Abrams et al. |
| 2002/0058966 A1 | 5/2002 | Tormala et al. | | 2004/0138747 A1 | 7/2004 | Kaladelfos |
| 2002/0077659 A1 | 6/2002 | Johnson et al. | | 2004/0143344 A1 | 7/2004 | Malaviya et al. |
| 2002/0099411 A1 | 7/2002 | Bartlett | | 2004/0147932 A1 | 7/2004 | Burkinshaw et al. |
| 2002/0111653 A1 | 8/2002 | Foerster | | 2004/0153103 A1 | 8/2004 | Schwartz et al. |
| 2002/0120270 A1 | 8/2002 | Trieu et al. | | 2004/0153153 A1 | 8/2004 | Elson et al. |
| 2002/0120292 A1 | 8/2002 | Morgan | | 2004/0162579 A1 | 8/2004 | Foerster |
| 2002/0123752 A1 | 9/2002 | Schultheiss et al. | | 2004/0166169 A1 | 8/2004 | Malaviya et al. |
| 2002/0128654 A1 | 9/2002 | Steger et al. | | 2004/0182968 A1 | 9/2004 | Gentry |
| 2002/0128684 A1 | 9/2002 | Foerster | | 2004/0187314 A1 | 9/2004 | Johnson |
| 2002/0129820 A1 | 9/2002 | Ryan et al. | | 2004/0199169 A1 | 10/2004 | Koons et al. |
| 2002/0143336 A1 | 10/2002 | Hearn | | 2004/0204722 A1 | 10/2004 | Sikora et al. |
| 2002/0147463 A1 | 10/2002 | Martinek | | 2004/0220574 A1 | 11/2004 | Pelo et al. |
| 2002/0161401 A1 | 10/2002 | Steiner | | 2004/0225292 A1 | 11/2004 | Sasso et al. |
| 2002/0161439 A1 | 10/2002 | Strobel et al. | | 2004/0225305 A1* | 11/2004 | Ewers et al. ............... 606/153 |
| 2002/0165548 A1 | 11/2002 | Jutley | | 2004/0236353 A1 | 11/2004 | Bain et al. |
| 2002/0169452 A1 | 11/2002 | Tormala et al. | | 2004/0236373 A1 | 11/2004 | Anspach |
| 2002/0169477 A1 | 11/2002 | Demopulos et al. | | 2004/0243139 A1 | 12/2004 | Lewis et al. |
| 2002/0169478 A1 | 11/2002 | Schwartz et al. | | 2004/0243178 A1 | 12/2004 | Haut et al. |
| 2002/0173788 A1 | 11/2002 | Bojarski et al. | | 2004/0243235 A1 | 12/2004 | Goh et al. |
| 2002/0188298 A1 | 12/2002 | Chan | | 2004/0249394 A1 | 12/2004 | Morris et al. |
| 2002/0193830 A1 | 12/2002 | Bonutti | | 2004/0267164 A1 | 12/2004 | Rhodes et al. |
| 2003/0023268 A1 | 1/2003 | Lizardi | | 2004/0267265 A1 | 12/2004 | Kyle |
| 2003/0032961 A1 | 2/2003 | Pelo et al. | | 2004/0267270 A1 | 12/2004 | Jacobs et al. |
| 2003/0033021 A1 | 2/2003 | Plouhar et al. | | 2004/0267276 A1 | 12/2004 | Camino et al. |
| 2003/0033022 A1 | 2/2003 | Plouhar et al. | | 2004/0267277 A1 | 12/2004 | Zannis et al. |
| 2003/0036797 A1 | 2/2003 | Malaviya et al. | | 2004/0267286 A1 | 12/2004 | Gao et al. |
| 2003/0036801 A1 | 2/2003 | Schwartz et al. | | 2004/0267304 A1 | 12/2004 | Zannis et al. |
| 2003/0065391 A1 | 4/2003 | Re et al. | | 2004/0267309 A1 | 12/2004 | Garvin |
| 2003/0078585 A1 | 4/2003 | Johnson et al. | | 2005/0021087 A1 | 1/2005 | Koseki |
| 2003/0078603 A1 | 4/2003 | Schaller et al. | | 2005/0027307 A1 | 2/2005 | Schwartz et al. |
| 2003/0078617 A1 | 4/2003 | Schwartz et al. | | 2005/0033363 A1 | 2/2005 | Bojarski et al. |
| 2003/0083662 A1 | 5/2003 | Middleton | | 2005/0038426 A1 | 2/2005 | Chan |
| 2003/0083694 A1 | 5/2003 | Miller | | 2005/0055027 A1 | 3/2005 | Yeung et al. |
| 2003/0088251 A1 | 5/2003 | Braun et al. | | 2005/0055037 A1 | 3/2005 | Fathauer |
| 2003/0088272 A1 | 5/2003 | Smith | | 2005/0064042 A1 | 3/2005 | Vunjak-Novakovic et al. |
| 2003/0105477 A1 | 6/2003 | Schwartz et al. | | 2005/0065521 A1 | 3/2005 | Steger et al. |
| 2003/0105489 A1 | 6/2003 | Eichhorn et al. | | 2005/0070928 A1 | 3/2005 | Heino et al. |
| 2003/0120309 A1 | 6/2003 | Colleran et al. | | 2005/0074495 A1 | 4/2005 | Schwartz et al. |
| 2003/0130694 A1 | 7/2003 | Bojarski et al. | | 2005/0085819 A1 | 4/2005 | Ellis et al. |
| 2003/0130695 A1 | 7/2003 | McDevitt et al. | | 2005/0090828 A1 | 4/2005 | Alford |
| 2003/0135214 A1 | 7/2003 | Fetto et al. | | 2005/0090862 A1 | 4/2005 | McDevitt et al. |
| 2003/0135239 A1 | 7/2003 | Gabriel et al. | | 2005/0096696 A1 | 5/2005 | Forsberg |
| 2003/0135963 A1 | 7/2003 | Holbrook et al. | | 2005/0096697 A1 | 5/2005 | Forsberg et al. |
| 2003/0152522 A1 | 8/2003 | Miller et al. | | 2005/0096743 A1 | 5/2005 | Schmieding et al. |
| 2003/0153947 A1 | 8/2003 | Koseki | | 2005/0101957 A1 | 5/2005 | Buskirk et al. |
| 2003/0167072 A1 | 9/2003 | Oberlander | | 2005/0107795 A1 | 5/2005 | Morris et al. |
| 2003/0167090 A1 | 9/2003 | Chervitz et al. | | 2005/0107828 A1 | 5/2005 | Reese |
| 2003/0171811 A1 | 9/2003 | Steiner et al. | | 2005/0119531 A1 | 6/2005 | Sharratt |
| 2003/0176865 A1 | 9/2003 | Supinski | | 2005/0119696 A1 | 6/2005 | Walters et al. |
| 2003/0176919 A1 | 9/2003 | Schmieding | | 2005/0124996 A1 | 6/2005 | Hearn |
| 2003/0181925 A1 | 9/2003 | Bain et al. | | 2005/0125036 A1 | 6/2005 | Roby |
| 2003/0195528 A1 | 10/2003 | Ritchart | | 2005/0125073 A1 | 6/2005 | Orban et al. |
| 2003/0195564 A1 | 10/2003 | Tran et al. | | 2005/0131413 A1 | 6/2005 | O'Driscoll et al. |
| 2003/0208210 A1 | 11/2003 | Dreyfuss et al. | | 2005/0137600 A1 | 6/2005 | Jacobs et al. |
| 2003/0212456 A1 | 11/2003 | Lipchitz et al. | | 2005/0137624 A1 | 6/2005 | Fallman |
| 2003/0220660 A1 | 11/2003 | Kortenbach et al. | | 2005/0149033 A1 | 7/2005 | McGuire et al. |
| 2003/0225459 A1 | 12/2003 | Hammer et al. | | 2005/0149122 A1 | 7/2005 | McDevitt et al. |
| 2004/0002734 A1 | 1/2004 | Fallin et al. | | 2005/0149187 A1 | 7/2005 | Clark et al. |
| 2004/0006345 A1 | 1/2004 | Vlahos et al. | | 2005/0159812 A1 | 7/2005 | Dinger et al. |
| 2004/0006346 A1 | 1/2004 | Holmen et al. | | 2005/0165416 A1 | 7/2005 | Bojarski et al. |
| 2004/0015171 A1 | 1/2004 | Bojarski et al. | | 2005/0165482 A1 | 7/2005 | Goldhahn et al. |
| 2004/0015172 A1 | 1/2004 | Biedermann et al. | | 2005/0187565 A1 | 8/2005 | Baker et al. |
| 2004/0024456 A1 | 2/2004 | Brown et al. | | 2005/0187577 A1 | 8/2005 | Selvitelli et al. |
| 2004/0024457 A1 | 2/2004 | Boyce et al. | | 2005/0187635 A1 | 8/2005 | Metzger |
| 2004/0044391 A1* | 3/2004 | Porter ............... 623/1.1 | | 2005/0203620 A1 | 9/2005 | Steiner et al. |
| 2004/0059357 A1 | 3/2004 | Koseki | | 2005/0222618 A1 | 10/2005 | Dreyfuss et al. |
| 2004/0087981 A1 | 5/2004 | Berube et al. | | 2005/0222619 A1 | 10/2005 | Dreyfuss et al. |
| 2004/0092936 A1 | 5/2004 | Miller et al. | | 2005/0228448 A1* | 10/2005 | Li ............... 606/232 |
| 2004/0093032 A1 | 5/2004 | Sinnott et al. | | 2005/0240198 A1 | 10/2005 | Albertson et al. |
| 2004/0098051 A1 | 5/2004 | Fallin et al. | | 2005/0251177 A1 | 11/2005 | Saadat et al. |
| 2004/0098053 A1 | 5/2004 | Tran | | 2005/0251208 A1* | 11/2005 | Elmer et al. ............... 606/232 |
| 2004/0111117 A1 | 6/2004 | Colleran et al. | | 2005/0251210 A1 | 11/2005 | Westra et al. |
| 2004/0122431 A1 | 6/2004 | Biedermann et al. | | 2005/0267479 A1 | 12/2005 | Morgan et al. |
| 2004/0133206 A1 | 7/2004 | Stevens et al. | | 2005/0267533 A1 | 12/2005 | Gertner |

| | | |
|---|---|---|
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1* | 1/2006 | Nobis et al. ............... 606/232 |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1* | 3/2007 | Schwartz ............... 623/1.39 |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0248091 A1 | 10/2009 | Teague et al. |
| 2009/0265014 A1 | 10/2009 | May et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |

| | | | |
|---|---|---|---|
| 2011/0218625 A1 | 9/2011 | Berelsman et al. | |
| 2011/0224799 A1 | 9/2011 | Stone | |
| 2011/0264141 A1 | 10/2011 | Denham et al. | |
| 2011/0270278 A1 | 11/2011 | Overes et al. | |
| 2011/0270306 A1 | 11/2011 | Denham et al. | |
| 2012/0041485 A1 | 2/2012 | Kaiser et al. | |
| 2012/0041486 A1 | 2/2012 | Stone et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0059418 A1 | 3/2012 | Denham et al. | |

FOREIGN PATENT DOCUMENTS

| | | |
|---|---|---|
| AU | 440266 | 10/1967 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2009012021 A1 | 1/2009 |

OTHER PUBLICATIONS

"EZ Loc Femoral Fixation Device," copyright 2005 Arthrotek, Inc. (8 sheets).

"Make your next tendon repair an open-and-shut case. The Teno Fix® Tendon Repair System", Teno Fix® brochure, 2003 (2 pages) Ortheon® Medical.

"PANALOK Anchor with PDS II and ETHIBOND Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-Journal 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Bio-Intrafix (TCP/PLA & Intrafix, Tibial Soft Tissue Fasteners, by DePuy Mitek, 6 sheets, (date unknown).

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 (Oct. 2002): pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

Invitation to Pay Additional Fees mailed Jun. 9, 2011 for PCT/US2001/026349 claiming benetif of U.S. Appl. No. 12/938,902, filed Nov. 3, 2010; and U.S. Appl. No. 12/719,337, filed Mar. 8, 2010.

"AperFix® System Surgical Technique Guide. Single Tunnel Double Bundle.™" Cayenne Medical brochure. (Aug. 2008) 8 sheets.

"Bio-Intrafix Tibial Soft Tissue Fasteners, Building on the Legacy of IntraFix," brochure. DePuy Mitek,(Feb. 2007) 6 sheets.

"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.

"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . ." Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.

"Arthroscopic Meniscal Repair using the Meniscal Cinch™", Surgical Technique brochure. (2008) Arthrex® 6 sheets.

Pioneer® Sternal Cable System (2010).

Rapid Sternal Closure (2006) KLS Martin L.P. http://www.rapidstemalclosure.com/medical/demo.php Web accessed Sep. 8, 2008.

Saxena, Pankaj, MCh, DNB et al., "Use of Double Wires in Sternal Closure, A Useful Technique," Texas Heart® Institute. Journal List>Tex Heart Inst J > v.33(4); (2006).

Zeitani, Jacob, M.D., "A New Sternal Reinforcement Device to Prevent and Treat Sternal Dehiscence," CTSNet.org (Jun. 30, 2008).

US 6,238,418, 05/2001, Schwartz et al. (withdrawn)

* cited by examiner

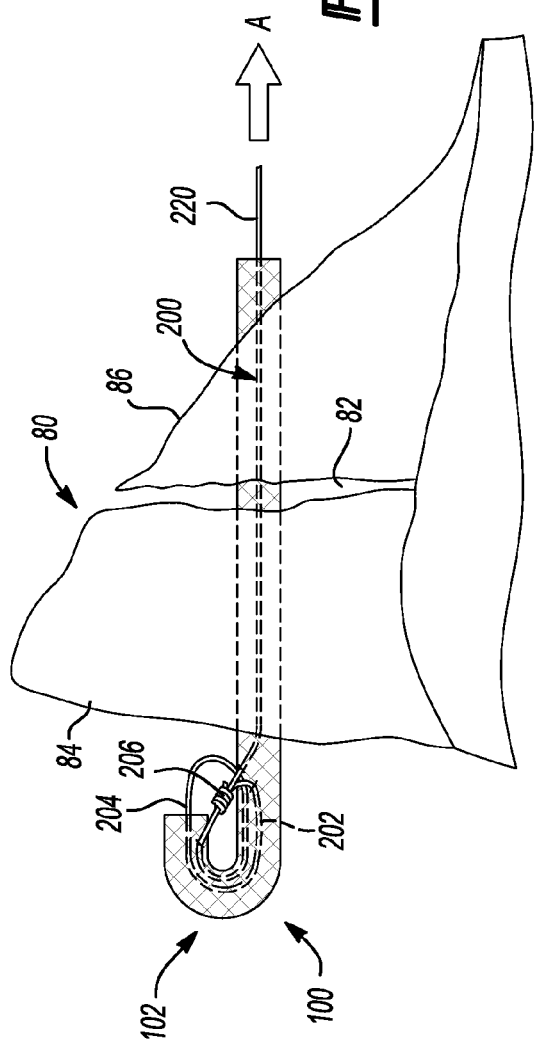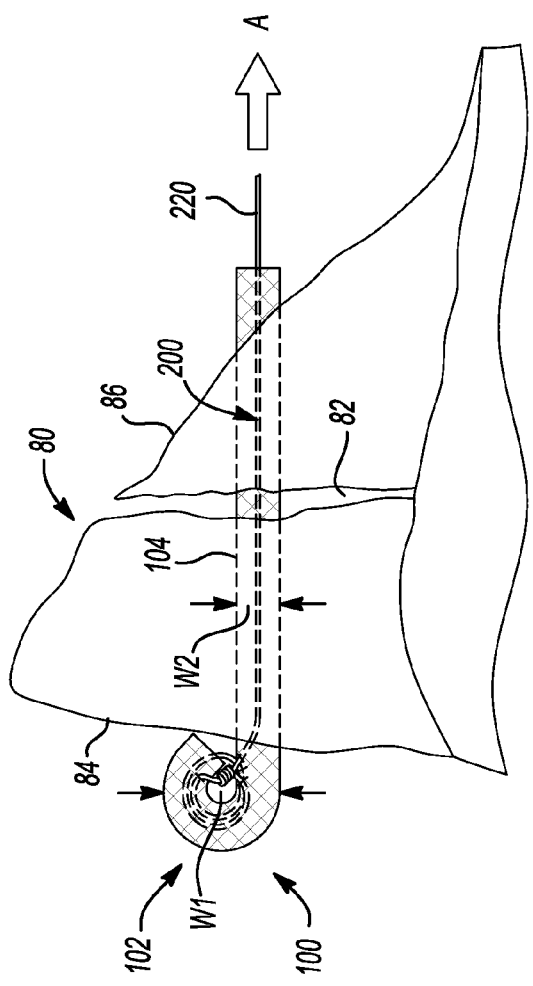

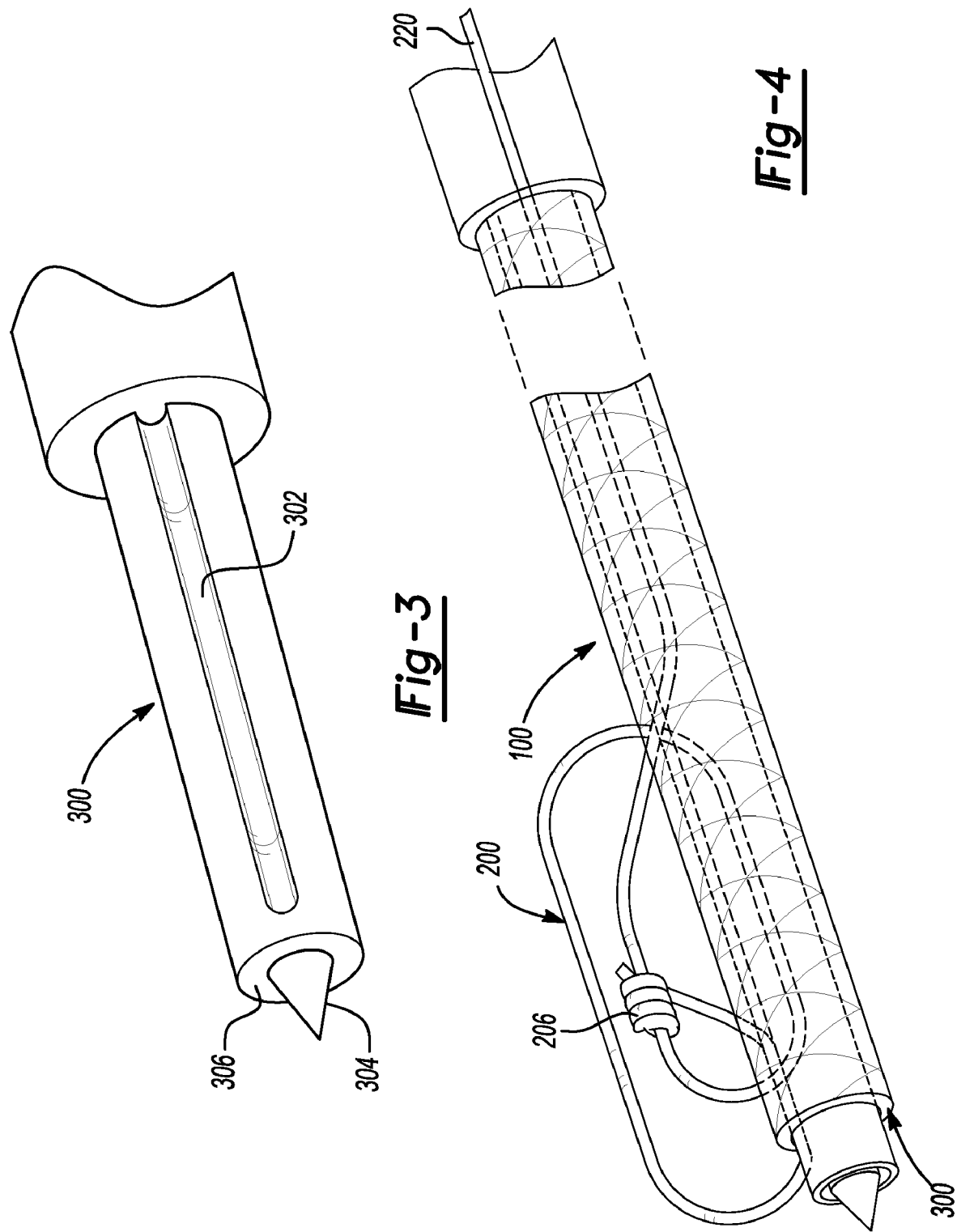

SOFT TISSUE REPAIR AND CONDUIT DEVICE

CROSS-REFERENCE TO RELATED APPLICATIONS

This application is a continuation of U.S. patent application Ser. No. 11/869,440 filed Oct. 9, 2007, now U.S. Pat. No. 7,857,830 issued Dec. 28, 2010, which claims the benefit of U.S. Provisional Application No. 60/885,062, filed on Jan. 16, 2007, and U.S. Provisional Application No. 60/885,057, filed on Jan. 16, 2007, and which is a continuation-in-part of U.S. patent application Ser. No. 11/347,661 filed Feb. 3, 2006, now U.S. Pat. No. 7,749,250 issued Jul. 6, 2010, and a continuation-in-part of Ser. No. 11/408,282 filed on Apr. 20, 2006, now abandoned. The disclosures of the above applications are incorporated herein by reference.

INTRODUCTION

Tears caused by trauma or disease in soft tissue, such as cartilage, ligament, or muscle, can be repaired by suturing and/or use of various fixation devices. Various tissue fixation devices have been developed for facilitating suturing and are effective for their intended purposes.

The present teachings provide a soft tissue repair and conduit device for repairing soft tissue defects and providing a conduit for facilitating healing and promoting soft tissue vascularity.

SUMMARY

The present teachings provide a soft tissue repair method. The method includes providing a flaccid tubular member having a longitudinal bore and first and second ends, the tubular member defining first and second portions integral with the tubular member. The method includes coupling the tubular member to a flexible strand, inserting the tubular member from a first side of the soft tissue to a second side of soft tissue such that a first portion of the tubular member exits the second side of the soft tissue and a second portion of the tubular member remains inside the soft tissue, tensioning the flexible strand, deforming the first portion of the tubular member to an anchoring shape, and forming a vascularization conduit from the second portion of the tubular member.

In another aspect, the soft tissue repair method includes inserting a flaccidly deformable tubular member through a meniscus, the tubular member having first and second portions, traversing a meniscal defect with the second portion, and anchoring the tubular member to an outer surface of the meniscus with the first portion of the tubular member.

In a further aspect, the soft tissue repair method includes passing a shaft of an inserter through a longitudinal bore of a flaccidly deformable tubular member, inserting the deformable tubular member axially through soft tissue until a first portion of the tubular member is outside an outer surface of the soft tissue and a remaining portion extends axially inside the soft tissue, and deforming the first portion into an anchor on the outer surface of the soft tissue.

The present teachings further provide a soft tissue repair device includes a deformable tubular member having a longitudinal bore extending between first and second open ends and a flexible strand passing through the longitudinal bore of the tubular member. The flexible strand has a first end portion extending outside the first open end of the tubular member and a second portion forming a first loop that passes through the second open end of the tubular member and an intermediate opening between the first and second open ends of the tubular member. Pulling the first end portion of the flexible strand away from the tubular member deforms a portion of the tubular member between the second open end and the intermediate opening into a folded shape forming a soft tissue anchor. The flexible strand can include a second loop and have a second end coupled the second loop with a slipknot. The tubular member can be made of harvested vascular material or other natural or synthetic biocompatible material.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 2C is an environmental side view illustrating tensioning a flexible strand to deform the first portion of the tubular member;

FIG. 2D is an environmental side view illustrating further tensioning a flexible strand to form an anchor from the first portion of the tubular member;

FIG. 3 is a perspective view of an inserter according to the present teachings; and FIG. 4 is a perspective view of a flexible tubular member loaded on the inserter of FIG. 3.

DESCRIPTION OF VARIOUS ASPECTS

The following description is merely exemplary in nature and is in no way intended to limit the present teachings, applications, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic or other procedures.

Figure 1:
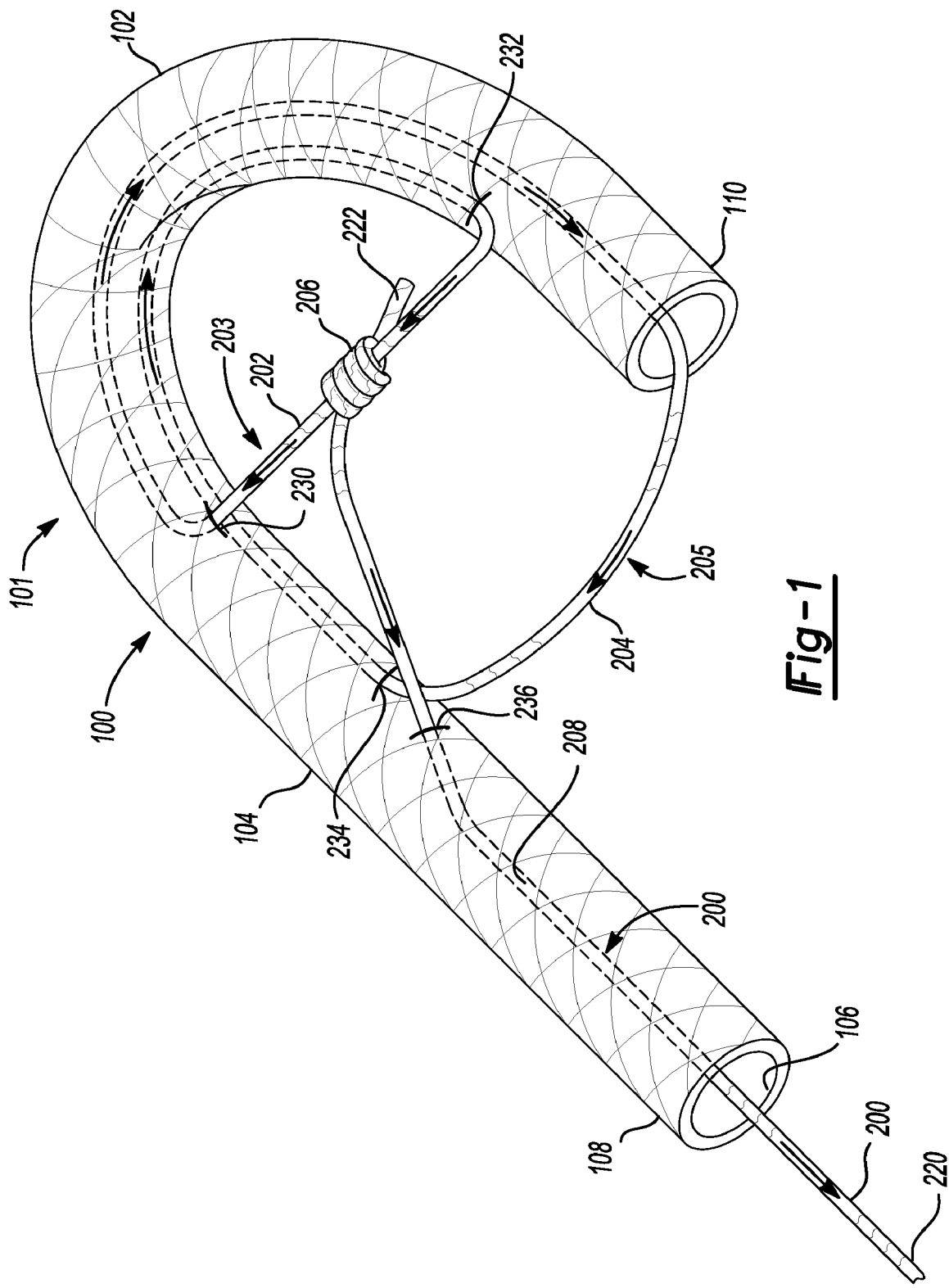
FIG. 1 is a perspective view of a flexible tubular member coupled to a flexible strand according to the present teachings, the tubular member shown with a first portion deformed.

An exemplary soft tissue repair device 101 according to the present teachings is illustrated in FIG. 1. The repair device 101 can include an elongated flexible member 100 in the form of a flaccid and deformable hollow sleeve or tubular member with a longitudinal inner bore 106 and first and second ends 108, 110. The repair device 101 can also include an elongated flexible strand 200, such as a suture, coupled to the flexible member 100. The flexible strand 200 can have first and second ends 220, 222.

The flexible member 100 can be made of resorbable or non-resorbable materials, including braided suture, woven/braided from biocompatible materials or fibers, such as, for example, polymer, polyester, polyethylene, cotton, silk, harvested vascular structures, or other natural or synthetic materials. The flexible member 100 can have any properties that allow the flexible member 100 to change shape or deform. The flexible member 100 can be, for example, compliant, flexible, foldable, squashable, squeezable, deformable, limp, flaccid, elastic, low-modulus, soft, spongy, perforated or any other flexible member which can change shape.

In some aspects, the flexible member 100 can be coated with biological or biocompatible coatings, and it can also be soaked in platelets and other biologics, which can be easily absorbed by the flexible member 100 in particular when, for example, the flexible member 100 is made from spongy, absorbent material. It should be understood by the above description that the flexible member 100 cannot pierce or otherwise penetrate tissue either with the first and second ends 108, 110 or with any portion thereof. The strand member 200 can be made of braided filaments or fibers of biocompatible material, including natural and synthetic fibers, such as cotton, silk, polymer, polyester, polyethylene, suture, and other materials.

Referring to FIGS. 3 and 4, the flexible member 100 can be loaded on the external surface of an inserter 300. The inserter 300 can include a shaft portion 302 and pointed or sharp tip 304. The inserter 300 can pass through the longitudinal inner bore 106 of the flexible member 100, as shown in FIG. 4, for guiding the flexible member 100 through soft tissue. Other inserters can also be used, such as, for example, the inserters described in the above cross-referenced and incorporated by reference patent applications, for example. The inserter 300 can include an external longitudinal guiding groove 302 for guiding a portion of the strand member 200.

The strand member 200 can be coupled to the flexible member 100 such that tensioning the strand member 200 by pulling on a free end 220 of the strand member 200 causes a first portion 102 of the flexible member to deform to a U-shape, as shown in FIG. 2C. Further tensioning of the strand member 200 causes the first portion 102 to deform to a bulkier, bunched-up, ball-like shape or anchoring shape that can serve as an anchor outside soft tissue 80, as shown in FIG. 2D and discussed below. The anchoring shape of the first portion 102 has a width W1 that is greater that the width W2 of the second portion 104 and of the opening formed in the tissue by the introduction of the flexible member 100 into the tissue 80, and prevents the first portion 102 of the flexible member 100 from re-entering the soft tissue and be pulled through the incision, thereby anchoring the flexible member 100 to the soft tissue 80. The remaining second portion 104 of the flexible member 100 can remain elongated with a substantially straight or curved or tortuous shape that forms a vascularization conduit bridging a soft tissue defect 82, and/or providing a vascularization path between vascular and avascular portions of the soft tissue 80, as discussed below.

An exemplary aspect of coupling the strand member 200 to the flexible member 100 to deform the first portion 102 is illustrated in FIG. 1, after partial tensioning. The strand member 200 can define intersecting and reducible-length loops 203, 205 passing through the inner bore 106 of the flexible member 100 and having external segments 202, 204. The first external segment 202 can extend outside the bore 106 from openings 230, 232 of the flexible member 100. The second external segment 204 can extend outside the bore 106 from an opening 234 to the opening at the second end 110 of the flexible member 100. The first end 220 of the strand member 200 can exit through the opening of the first end 106 of the flexible member 100, and the second end 222 of the strand member 200 can be coupled to the first external segment 202 with a slip knot 206. Tensioning the strand member 200 by pulling the first end 220 of the strand member 200 can reduce the length the external segments 202, 204 and associated strand loops 203, 205 allowing the first portion 102 to deform to the shape shown in FIG. 2D. A third segment 208 of the strand member 200 can extend through the inner bore 106 along the second portion 104 from an opening 236 to the opening of the first end 108 of the flexible member 100.

Figure 2A:
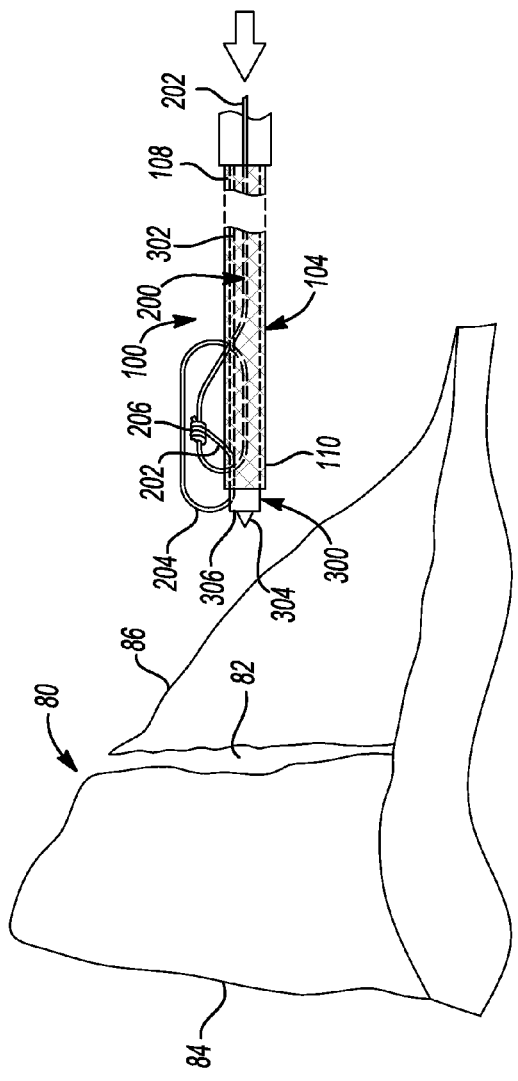
FIG. 2A is an environmental side view illustrating a flexible tubular member loaded on an inserter for insertion through soft tissue.
Figure 2B:
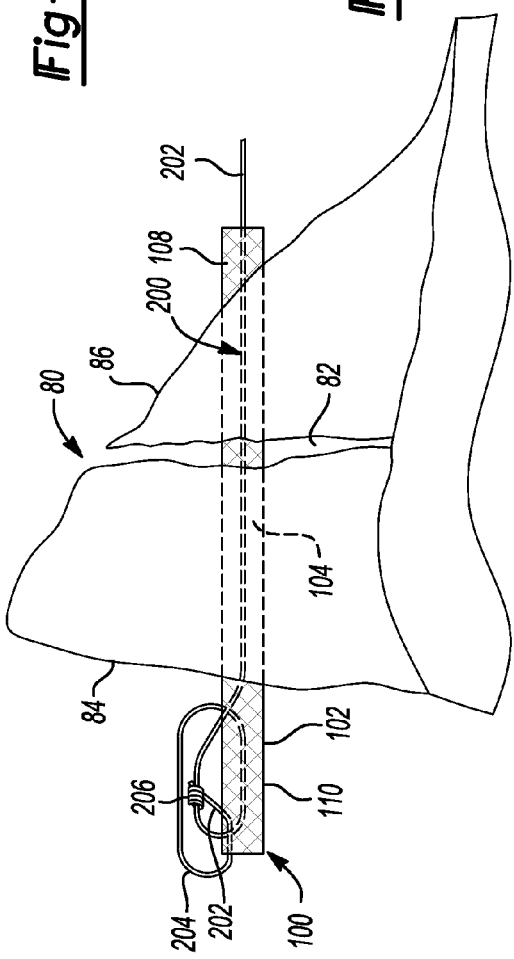
FIG. 2B is an environmental side view illustrating a flexible tubular member inserted through soft tissue such that a first portion of the tubular member is outside an outer surface of the soft tissue.
Figure 2E:
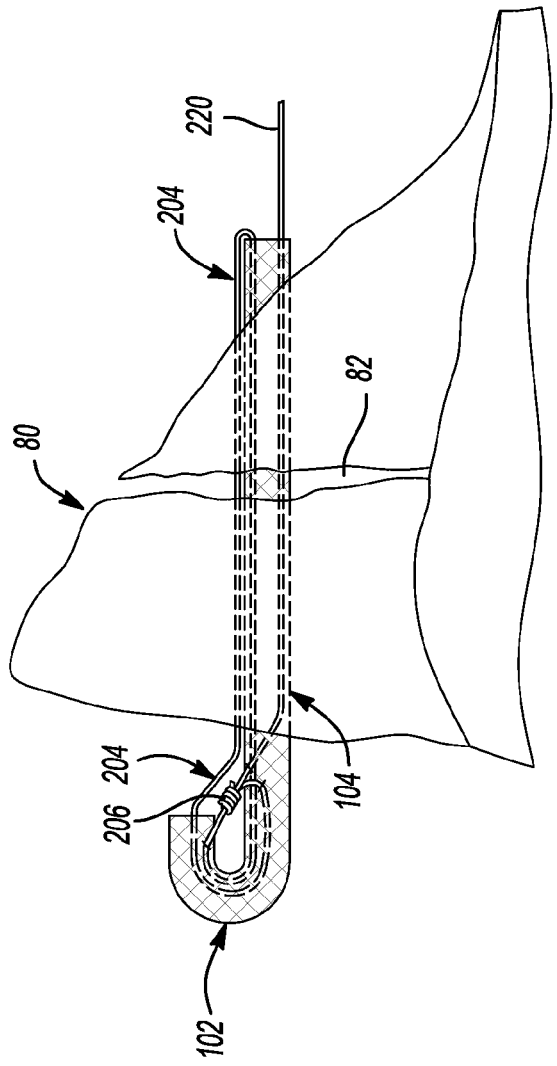
FIG. 2E is an environmental side view illustrating tensioning a flexible strand to deform the first portion of the tubular member.
Figure 2F:
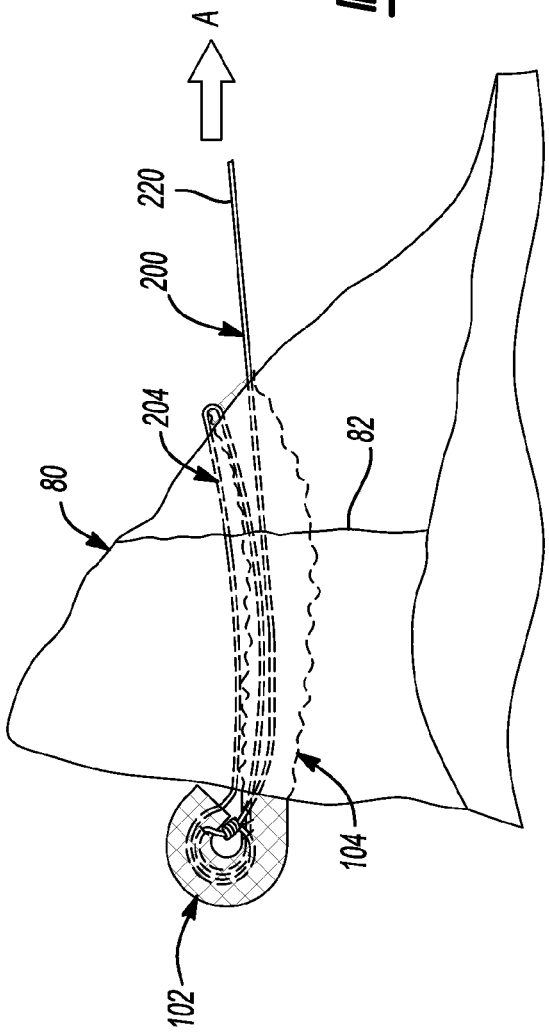
FIG. 2F is an environmental side view illustrating further tensioning of the flexible strand of FIG. 2D to form an anchor from the first portion of the tubular member.

An alternative aspect of coupling the strand member 200 to the flexible member 100 to deform the first portion 102 is illustrated in FIGS. 2E-F. In this aspect, the second external segment 204 can extend between the first and second ends 108, 110 of the flexible member 100. Tensioning the strand member 220 can cause some curving of the second portion 104, as shown in FIG. 2F.

The soft tissue repair device 101 can be used to repair a soft tissue defect 82, such as, for example, a tear, or other weakness in fibrous soft tissue 80, such as in meniscal tissue, cartilage, muscle or other fibrous tissue under the skin. In the exemplary illustration of FIGS. 2A-2D, the soft-tissue repair assembly 100 is illustrated for meniscal repair and vascularization. The second portion 104 of the flexible member can serve as a conduit between vascular and avascular regions of the meniscus on opposite sides of the defect 82 for conducting native or endogenous biological materials between first and second areas of the tissue, such as, for example, between healthy tissue and injured or torn tissue, or between areas of different vascularity, such as between red-red (vascular), red-white (semi-vascular) and white (avascular) tissue areas of a meniscus. The second portion 104 can provide a vascularity path in the soft tissue 80 for facilitating healing or repair. Additionally, biological materials in the form of platelet gels can be deposited in the flexible member 100 before implantation, as another mechanism of biological material delivery, including nutrient material delivery.

The first portion 102 of the flexible member 100 can serve as an anchor implanted on an outer surface 84 of the soft tissue 80. The implanted shape of the first portion 102 of the flexible member 102 can be of a bulkier or ball-like shape with length to width ratio close to one, as illustrated in FIG. 2D, for snugly securing the flexible member 100 on the outer surface of the soft tissue 80. The implanted shape of the first portion 102 can have bigger overall width or enclosed cross-sectional area or volume than the second portion 104 such that the first portion 102 cannot be pulled out of the same opening through which it was originally inserted. The first portion 102 can retain its bulkier shape after implantation, even after the tension on the strand portion 106 is removed.

Referring to FIGS. 2A-2D, the repair device 101 can be loaded on the inserter 300 and passed from a first surface 86 of the soft tissue 80 through the defect 82 and again through the tissue 80 until the first portion 102 of the flexible member 100 is outside a second surface 84 of the soft tissue 80 in a substantially elongated (straight or curved) configuration, as shown in FIG. 2B. Tensioning the strand member 200 by pulling in the direction of arrow A, deforms the first portion 102 into its anchor-like bulkier shape, as shown in FIGS. 2C and 2D. The second portion 104 can remain elongated (straight or curved) and form a vascularization conduit for the soft tissue 80.

It will be appreciated that multiple soft tissue repair devices 101 can be used by repeating the above procedure for repairing a soft tissue defect as described in the patent applications cross-referenced above. The present teachings provide an easy to use and effective method for repairing soft tissue with an integral device that provides anchoring and vascularization upon implantation.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings as defined in the following claims.

What is claimed is:

1. A soft tissue repair device comprising:
a deformable tubular member having a longitudinal bore extending between first and second open ends of the tubular member; and
a flexible strand passing through the longitudinal bore of tubular member, the flexible strand having a first end portion extending outside the first open end of the tubular member and a second portion forming a first loop that passes through the second open end of the tubular member and an intermediate opening between the first and second open ends of the tubular member, such that pulling the first end portion of the flexible strand away from the tubular member deforms a second portion of the tubular member between the second open end and the intermediate opening into a folded shape forming a soft tissue anchor and maintains a remaining first portion between the intermediate opening and the first open end in a straight configuration.

2. The soft tissue repair device of claim 1, wherein the folded shape is U-shape.

3. The soft tissue repair device of claim 1, wherein the folded shape is a ball like shape.

4. The soft tissue repair device of claim 1, wherein the flexible strand forms a second loop.

5. The soft tissue repair device of claim 1, wherein the flexible strand includes a second end coupled the second loop with a slipknot.

6. The soft tissue repair device of claim 1, wherein the tubular member comprises harvested vascular material.

7. The soft tissue repair device of claim 1, wherein the tubular member comprises natural or synthetic biocompatible material.

8. The soft tissue repair device of claim 1, wherein the tubular member is a tubular braided suture.

9. A soft tissue repair device comprising:
a single deformable elongated tubular member having a first open end and a second open end and an intermediate point between the first and second open ends, the tubular member having a first portion between the first open end and the intermediate point and a second portion between the intermediate point and the second open end, wherein the first portion forms an elongated soft tissue vascularization conduit for fluidically connecting opposite sides of soft tissue to form a vascularization path, and wherein the second portion forms a deformable soft tissue anchor integral to the vascularization conduit; and
a flexible strand passing through the soft tissue anchor and configured to deform only the soft tissue anchor into a folded shape by tensioning the flexible strand while the first portion is maintained in a straight configuration, wherein the flexible strand forms first and second loops passing through a longitudinal bore extending between the first and second open ends of the tubular member.

10. The soft tissue repair device of claim 9, wherein the flexible strand passes through the vascularization conduit.

11. The soft tissue repair device of claim 9, wherein the folded shape is U-shaped.

12. The soft tissue repair device of claim 9, wherein the folded shape is ball-like.

13. The soft tissue repair device of claim 9, wherein the flexible strand has first and seconds ends, the first end extending out of the longitudinal bore for tensioning the flexible strand, and the second end forming a slipknot on the second loop.

14. The soft tissue repair device of claim 13, wherein the first loop passes through the longitudinal bore between the second open end and a first opening through a sidewall of the tubular member and intermediate between the first and second open ends.

15. The soft tissue repair device of claim 14, wherein the second loop passes through second and third openings through the sidewall of the tubular member and intermediate between the first and second open ends.

16. The soft tissue repair device of claim 9, wherein the tubular member comprises harvested vascular material.

17. The soft tissue repair device of claim 9, wherein the tubular member comprises natural or synthetic biocompatible material.

18. The soft tissue repair device of claim 9, wherein the tubular member is a tubular braided suture.

19. A soft tissue repair device comprising:
a deformable tubular member having a longitudinal bore extending between first and second open ends of the tubular member; and
a flexible strand having first and second ends, the flexible strand forming first and second intersecting loops, the first loop passing through a first portion of the longitudinal bore between the second open end and a first opening through a sidewall of the tubular member and intermediate between the first and second open ends, the second loop passing through a second portion of the longitudinal bore between second and third openings through the sidewall of the tubular member and intermediate between the first and second open ends, the first end of the flexible strand extending through the longitudinal bore from the first opening and out the first open end, the second end of the flexible strand forming a slipknot with the second loop, such that pulling the first end deforms a second portion of the tubular member between the second open end and the first opening into a folded shape forming a soft tissue anchor and maintains a remaining first portion between the first opening and the first open end in a straight configuration.

20. The soft tissue repair device of claim 19 wherein the tubular member comprises harvested vascular material.

21. The soft tissue repair device of claim 19, wherein the tubular member comprises natural or synthetic biocompatible material.

22. The soft tissue repair device of claim 19, wherein the tubular member is a tubular braided suture.

* * * * *

UNITED STATES PATENT AND TRADEMARK OFFICE
CERTIFICATE OF CORRECTION

PATENT NO. : 8,273,106 B2  
APPLICATION NO. : 12/976328  
DATED : September 25, 2012  
INVENTOR(S) : Kevin T. Stone et al.

Page 1 of 1

It is certified that error appears in the above-identified patent and that said Letters Patent is hereby corrected as shown below:

Title Page, (56), References Cited, Other Publications, page 12, Column 1, Reference No. 19, "benetif" should be --benefit--.

In the Specification

Column 1, line 61, insert --that-- before "includes".

Column 2, line 7, after "coupled" insert --to--.

Column 4, line 10, after "length" insert --of--.

Column 4, lines 45-46, "flexible member 102" should be --flexible member 100--.

In the Claims

Column 5, line 41, Claim 5, after "coupled" insert --to--.

Signed and Sealed this  
Twenty-second Day of October, 2013

Teresa Stanek Rea  
*Deputy Director of the United States Patent and Trademark Office*